(12) United States Patent
Lin et al.

(10) Patent No.: US 11,832,967 B2
(45) Date of Patent: Dec. 5, 2023

(54) WEARABLE PHYSIOLOGICAL SIGNAL DETECTING DEVICE

(71) Applicants: Ken-Ping Lin, Taipei (TW); Chih-Wen Chiang, Taipei (TW); Cheng-Ya Chi, Taipei (TW); Chien-Chu Chen, Taipei (TW)

(72) Inventors: Ken-Ping Lin, Taipei (TW); Chih-Wen Chiang, Taipei (TW); Cheng-Ya Chi, Taipei (TW); Chien-Chu Chen, Taipei (TW)

(73) Assignee: COMPAL ELECTRONICS, INC., Taipei (TW)

( * ) Notice: Subject to any disclaimer, the term of this patent is extended or adjusted under 35 U.S.C. 154(b) by 827 days.

(21) Appl. No.: 16/824,671

(22) Filed: Mar. 19, 2020

(65) Prior Publication Data

US 2021/0177354 A1 Jun. 17, 2021

(30) Foreign Application Priority Data

Dec. 16, 2019 (TW) .................................. 108145968

(51) Int. Cl.
*A61B 5/00* (2006.01)
*A61B 5/02* (2006.01)
(Continued)

(52) U.S. Cl.
CPC .......... *A61B 5/6831* (2013.01); *A61B 5/6844* (2013.01); *A61B 5/021* (2013.01);
(Continued)

(58) Field of Classification Search
None
See application file for complete search history.

(56) References Cited

U.S. PATENT DOCUMENTS

| 1,567,640 | A | * | 12/1925 | Guyot | ...................... | A44C 5/04 |
| | | | | | | 59/79.2 |
| 3,017,682 | A | * | 1/1962 | Vollet | ...................... | A44C 5/08 |
| | | | | | | 267/179 |

(Continued)

FOREIGN PATENT DOCUMENTS

WO 2017113319 7/2017

OTHER PUBLICATIONS

Oxford English Dictionary, definition of "telescoping", OED Third Edition 2016, retrieved from www.oed.com/view/Entry/37649376 (Year: 2016).*

(Continued)

*Primary Examiner* — Carl H Layno
*Assistant Examiner* — Manolis Pahakis
(74) *Attorney, Agent, or Firm* — JCIPRNET

(57) ABSTRACT

A wearable physiological signal detecting device includes a device main body and a telescopic structure. The device main body has a strap which surrounds to form a wearable space. The telescopic structure is disposed in the strap and has first surfaces and second surfaces. Each of the first surfaces faces the corresponding second surface. Each of the first surfaces and the corresponding second surface continuously move close and contact each other to assume a first state. The strap can be forced so that each of the first surfaces and the corresponding second surface move away from each other and have an angle to assume a second state. The size of the wearable space when the first surface and the corresponding second surface assume the second state is greater than the size of the wearable space when the first surface and the corresponding second surface assume the first state.

14 Claims, 9 Drawing Sheets

(51) Int. Cl.
*A61B 5/024* (2006.01)
*A61B 5/026* (2006.01)
*A61B 5/021* (2006.01)

(52) U.S. Cl.
CPC ........... *A61B 5/026* (2013.01); *A61B 5/02007* (2013.01); *A61B 5/02035* (2013.01); *A61B 5/02438* (2013.01)

(56) References Cited

U.S. PATENT DOCUMENTS

| | | | | |
|---|---|---|---|---|
| 3,307,347 | A * | 3/1967 | Christoff | A44C 5/08 59/79.1 |
| 3,590,576 | A * | 7/1971 | Rubinelli | A44C 5/04 59/79.1 |
| 3,601,977 | A * | 8/1971 | Kunzmann | A44C 5/04 224/175 |
| 3,786,629 | A * | 1/1974 | Rieth | A44C 5/08 59/79.1 |
| 4,723,406 | A * | 2/1988 | Ripley | A44C 5/08 59/79.3 |
| 4,823,562 | A * | 4/1989 | Yokote | A44C 5/04 224/267 |
| 4,999,990 | A * | 3/1991 | Wong | A44C 5/08 59/79.3 |
| 5,251,189 | A * | 10/1993 | Thorp | A44C 5/0007 379/430 |
| 5,615,179 | A * | 3/1997 | Yamamoto | G04G 17/06 224/168 |
| 6,205,622 | B1 * | 3/2001 | Odishoo | A44C 5/08 59/79.1 |
| 7,191,586 | B2 * | 3/2007 | Yamamoto | A44C 5/105 63/4 |
| 9,612,623 | B2 * | 4/2017 | Lim | H04M 1/0269 |
| 9,720,376 | B2 * | 8/2017 | Tsushima | G04G 17/06 |
| 10,037,053 | B2 * | 7/2018 | Malhotra | G06F 1/163 |
| 10,152,082 | B2 * | 12/2018 | Bailey | G06F 1/1656 |
| 10,416,713 | B2 * | 9/2019 | Wu | G06F 3/14 |
| 10,467,679 | B1 * | 11/2019 | Toumazou | G06F 1/1694 |
| 11,045,137 | B2 * | 6/2021 | Barbre | A61B 5/6801 |
| 11,481,031 | B1 * | 10/2022 | Anderson | G02B 27/0172 |
| 2003/0144586 | A1 * | 7/2003 | Tsubata | A61B 8/02 600/407 |
| 2005/0076674 | A1 * | 4/2005 | Frank | A44C 5/14 63/9 |
| 2005/0120746 | A1 * | 6/2005 | Winston | A44C 9/02 63/38 |
| 2010/0243688 | A1 * | 9/2010 | Gutierrez | A44C 5/025 224/175 |
| 2011/0199205 | A1 * | 8/2011 | Kreml | A61B 5/1118 340/539.11 |
| 2012/0083674 | A1 * | 4/2012 | Hidai | A61B 5/681 24/68 E |
| 2012/0253485 | A1 * | 10/2012 | Weast | G06F 1/163 700/91 |
| 2013/0106603 | A1 * | 5/2013 | Weast | G06F 1/163 340/539.11 |
| 2014/0078694 | A1 * | 3/2014 | Wissmar | H05K 7/06 361/749 |
| 2014/0268522 | A1 * | 9/2014 | Tanaka | A61B 5/0295 361/679.01 |
| 2014/0378113 | A1 * | 12/2014 | Song | G06F 3/014 455/418 |
| 2015/0089974 | A1 * | 4/2015 | Seo | A44C 5/0076 63/1.13 |
| 2015/0223574 | A1 * | 8/2015 | Nakamura | A44C 5/022 224/267 |
| 2016/0037874 | A1 * | 2/2016 | Webb | A45F 5/00 224/267 |
| 2016/0062410 | A1 * | 3/2016 | Ko | G06F 1/1681 361/679.03 |
| 2016/0157571 | A1 * | 6/2016 | Custer | A44C 5/0069 224/175 |
| 2016/0255944 | A1 * | 9/2016 | Baranski | A44C 5/2071 |
| 2016/0299526 | A1 * | 10/2016 | Inagaki | G06F 3/04883 |
| 2016/0357222 | A1 * | 12/2016 | Seo | G06F 1/1635 |
| 2017/0079386 | A1 * | 3/2017 | de Iuliis | G04B 37/1486 |
| 2017/0119314 | A1 * | 5/2017 | Just | A61B 5/681 |
| 2017/0164878 | A1 * | 6/2017 | Connor | G09B 19/00 |
| 2018/0042513 | A1 * | 2/2018 | Connor | A61B 5/6824 |
| 2018/0325451 | A1 * | 11/2018 | Liu | A61B 5/02055 |
| 2019/0033912 | A1 * | 1/2019 | Wu | G06F 1/163 |
| 2019/0034143 | A1 * | 1/2019 | Wu | G06F 3/14 |
| 2019/0050023 | A1 * | 2/2019 | Wu | A44C 5/0061 |
| 2019/0168071 | A1 * | 6/2019 | Franks | A61B 5/1072 |
| 2019/0302837 | A1 * | 10/2019 | Liao | A44C 5/0053 |
| 2020/0093015 | A1 * | 3/2020 | Seo | A61B 5/318 |
| 2021/0030123 | A1 * | 2/2021 | Wu | G06F 1/163 |
| 2022/0053892 | A1 * | 2/2022 | Al-Ali | A44C 5/107 |

OTHER PUBLICATIONS

"Office Action of Taiwan Counterpart Application", dated Apr. 19, 2021, p. 1-p. 5.

* cited by examiner

WEARABLE PHYSIOLOGICAL SIGNAL DETECTING DEVICE

CROSS-REFERENCE TO RELATED APPLICATION

This application claims the priority benefit of Taiwan application serial no. 108145968, filed on Dec. 16, 2019. The entirety of the above-mentioned patent application is hereby incorporated by reference herein and made a part of this specification.

BACKGROUND OF THE INVENTION

Field of the Invention

The disclosure relates to a wearable physiological signal detecting device, and in particular, to a wearable physiological signal detecting device which is convenient for a user to put on and take off.

Description of Related Art

Nowadays, with the advancement of science and technology, people often work and live at a fast pace, and as a result, health management is becoming increasingly important. People often use wearable physiological signal detecting devices to help manage their health. It is important to allow users to use the wearable physiological signal detecting devices conveniently and quickly. Therefore, how to improve the convenience of use of a wearable physiological signal detecting device is an issue to be addressed in this field.

SUMMARY OF THE INVENTION

The invention provides a wearable physiological signal detecting device which addresses the issue of inconvenience of use of the wearable physiological signal detecting device in the conventional art.

A wearable physiological signal detecting device of the invention includes a device main body and a telescopic structure. The device main body has a strap. The strap surrounds and forms a wearable space. The telescopic structure is disposed in the strap and has a plurality of first surfaces and a plurality of second surfaces. Each of the first surfaces faces the corresponding second surface. Each of the first surfaces and the corresponding second surface are adapted to continuously move close and contact each other to assume a first state. The strap is adapted to be forced so that each of the first surfaces and the corresponding second surface move away from each other and have an angle to assume a second state. A size of the wearable space when each of the first surfaces and the corresponding second surface assume the second state is greater than a size of the wearable space when each of the first surfaces and the corresponding second surface assume the first state.

In an embodiment of the invention, the telescopic structure includes a fixing member, a plurality of telescopic members, and a plurality of recovery members. The fixing member is disposed in the strap. The plurality of telescopic members are sequentially arranged and fixed to the fixing member. Each of the first surfaces is provided on one of two adjacent telescopic members, and each of the second surfaces is provided on the other one of the two adjacent telescopic members. The plurality of recovery members are respectively connected between two adjacent telescopic members and continuously provide elasticity so that each of the first surfaces and the corresponding second surface which are adjacent to each other assume the first state. A part of each of the recovery members is located between one of two adjacent telescopic members and the fixing member, and another part of each of the recovery members is located between the other one of the two adjacent telescopic members and the fixing member.

In an embodiment of the invention, each of the recovery members respectively includes a first fixing end and a second fixing end opposite to each other. The telescopic structure further includes a plurality of first fixing parts and a plurality of second fixing parts. The plurality of first fixing parts are respectively disposed on one of two adjacent telescopic members. Each of the first fixing ends is connected to the corresponding first fixing part and is located between the one of the two adjacent telescopic members and the fixing member. The plurality of second fixing parts are respectively disposed on the other one of the two adjacent telescopic members. Each of the second fixing ends is connected to the corresponding second fixing part and is located between the other one of the two adjacent telescopic members and the fixing member.

In an embodiment of the invention, the recovery member is a spring pin.

In an embodiment of the invention, the spring pin has an opening, and an angle of the opening is 120 degrees.

In an embodiment of the invention, the wearable physiological signal detecting device further includes a limiting structure. The limiting structure is disposed on the telescopic structure and is configured to limit a maximum value of the angle when each of the first surfaces and the corresponding second surface assume the second state.

In an embodiment of the invention, the telescopic structure includes a plurality of sequentially arranged telescopic members. Each of the first surfaces is provided on one of two adjacent telescopic members, and each of the second surfaces is provided on the other one of the two adjacent telescopic members. The limiting structure includes a plurality of groove blocks, a plurality of sliding blocks, a plurality of limiting columns, and a plurality of limiting grooves. The plurality of groove blocks are respectively disposed on each of the telescopic members. The plurality of sliding blocks are respectively disposed on one of two adjacent telescopic members. The plurality of limiting columns are respectively disposed to the corresponding sliding block. The plurality of limiting grooves are respectively provided in the groove block located on the other one of the two adjacent telescopic members. Each of the limiting columns is movably disposed in the corresponding limiting groove to limit the maximum value of the angle when each of the first surfaces and the corresponding second surface assume the second state.

In an embodiment of the invention, each of the limiting grooves is arc-shaped and defines a virtual center of circle. The virtual center of circle is located on an outer surface of the strap.

In an embodiment of the invention, the angle is greater than 0 degrees and less than or equal to 25 degrees.

In an embodiment of the invention, an end of the strap is not in contact with the device main body and is at a gap from the device main body. A size of the gap when each of the first surfaces and the corresponding second surface assume the second state is greater than a size of the gap when each of the first surfaces and the corresponding second surface assume the first state.

In an embodiment of the invention, the device main body has a plurality of flexible bending parts. The flexible bending parts are respectively disposed on the strap, are partially located in the wearable space, and respectively shield the first surface and the corresponding second surface which are adjacent to each other. A volume of each of the flexible bending parts located in the wearable space when each of the first surfaces and the corresponding second surface assume the first state is greater than a volume of each of the flexible bending parts located in the wearable space when each of the first surfaces and the corresponding second surface assume the second state.

In an embodiment of the invention, the device main body includes an outer frame and the strap connected to the outer frame. The wearable physiological signal detecting device further includes an electronic module and a sensing module. The strap is connected to the outer frame. The electronic module is connected to the outer frame and has a first sensor. The sensing module is connected to the outer frame and the electronic module and has a pair of second sensors and a hole. The hole communicates with the wearable space. The first sensor passes through the hole, and the first sensor and the pair of second sensors are partially located in the wearable space.

In an embodiment of the invention, a surface of the first sensor located in the wearable space and surfaces of the pair of second sensors located in the wearable space are flush with each other.

In an embodiment of the invention, the electronic module is fixed to the outer frame. The sensing module is fixed to the outer frame and the electronic module.

In an embodiment of the invention, the electronic module is fixed to the outer frame. The sensing module is detachably disposed on the outer frame and the electronic module.

In an embodiment of the invention, the electronic module is detachably disposed on the outer frame. The sensing module is detachably disposed on the outer frame and the electronic module.

Based on the above, the wearable physiological signal detecting device of the invention is convenient for a user to put on or take off.

To make the aforementioned more comprehensible, several embodiments accompanied with drawings are described in detail as follows.

DESCRIPTION OF THE EMBODIMENTS

Figure 1:
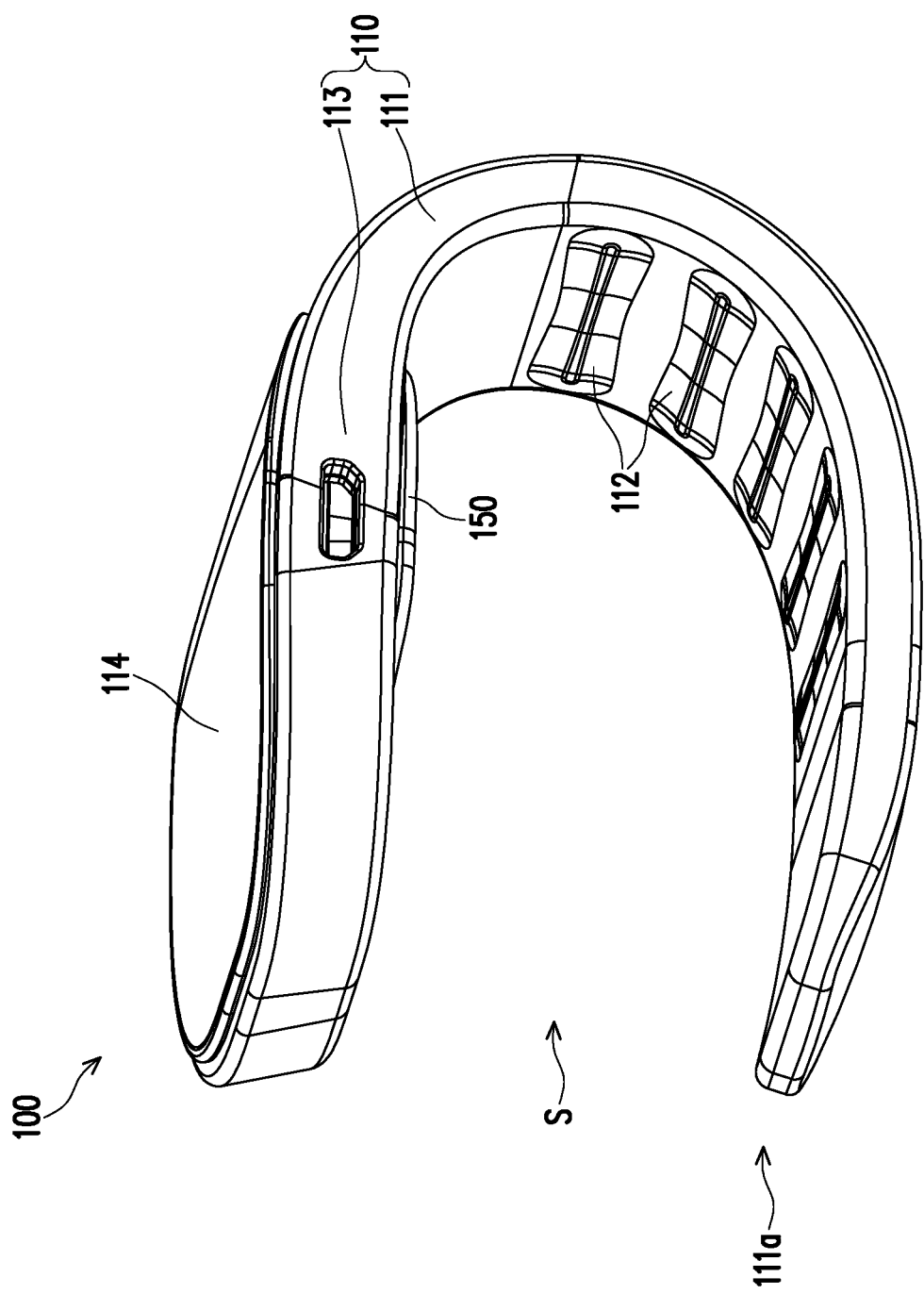
FIG. 1 is a schematic perspective view showing a wearable physiological signal detecting device according to an embodiment of the invention.
Figure 2:
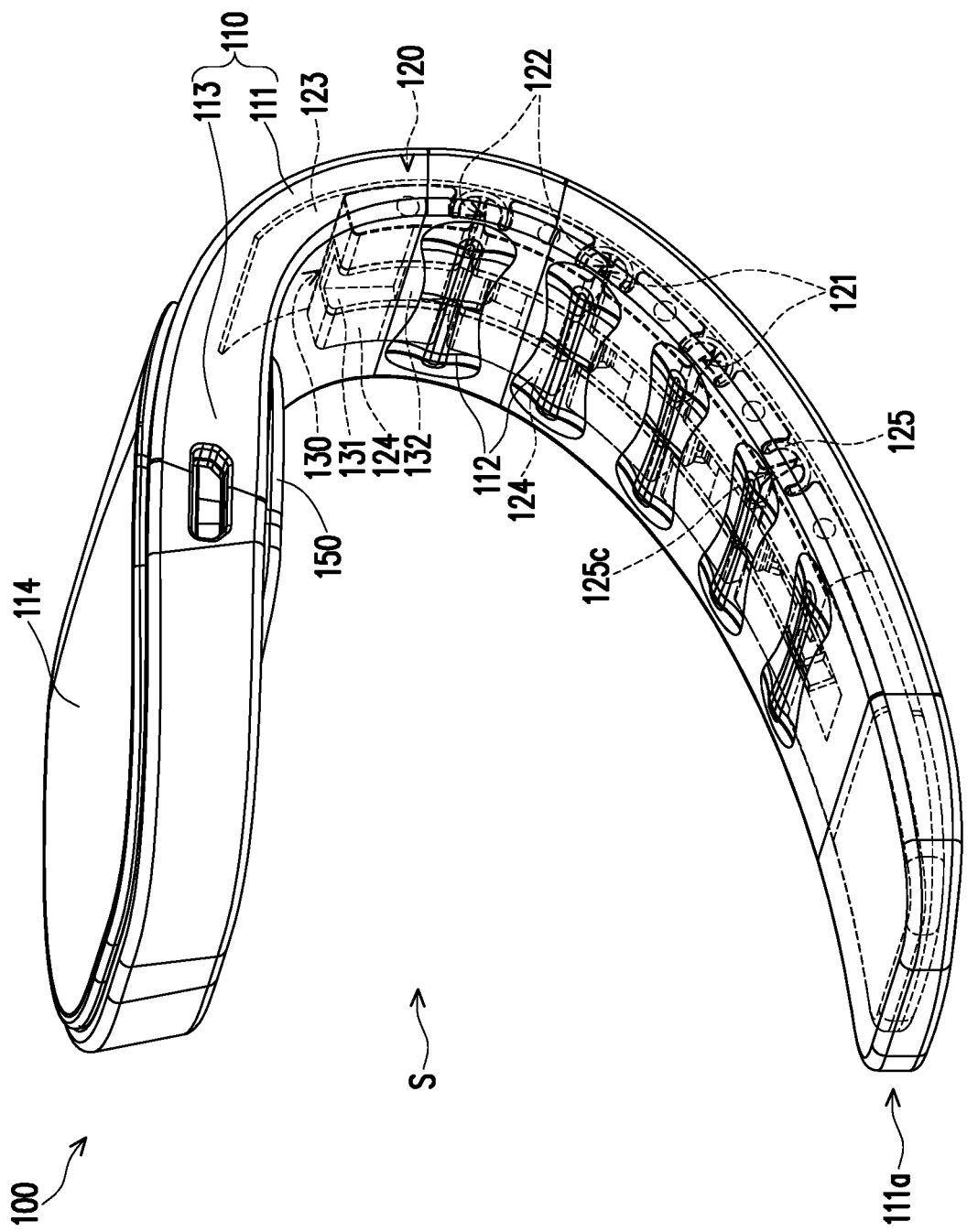
FIG. 2 is a schematic perspective view showing a first surface and a second surface of a telescopic structure of the wearable physiological signal detecting device of FIG. 1 in a second state.
Figure 3:
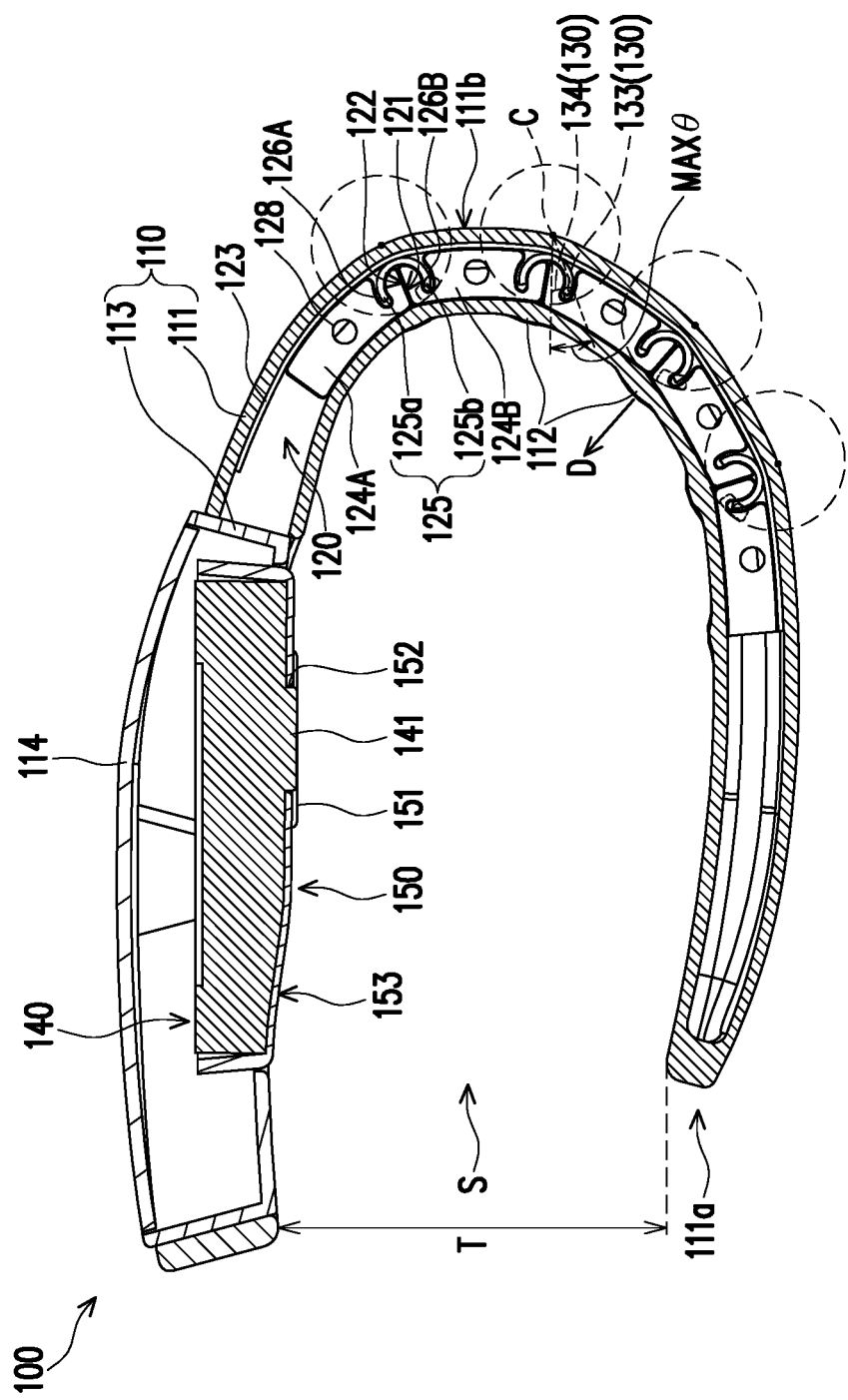
FIG. 3 is a schematic partial cross-sectional view showing the wearable physiological signal detecting device of FIG. 1.
Figure 4:
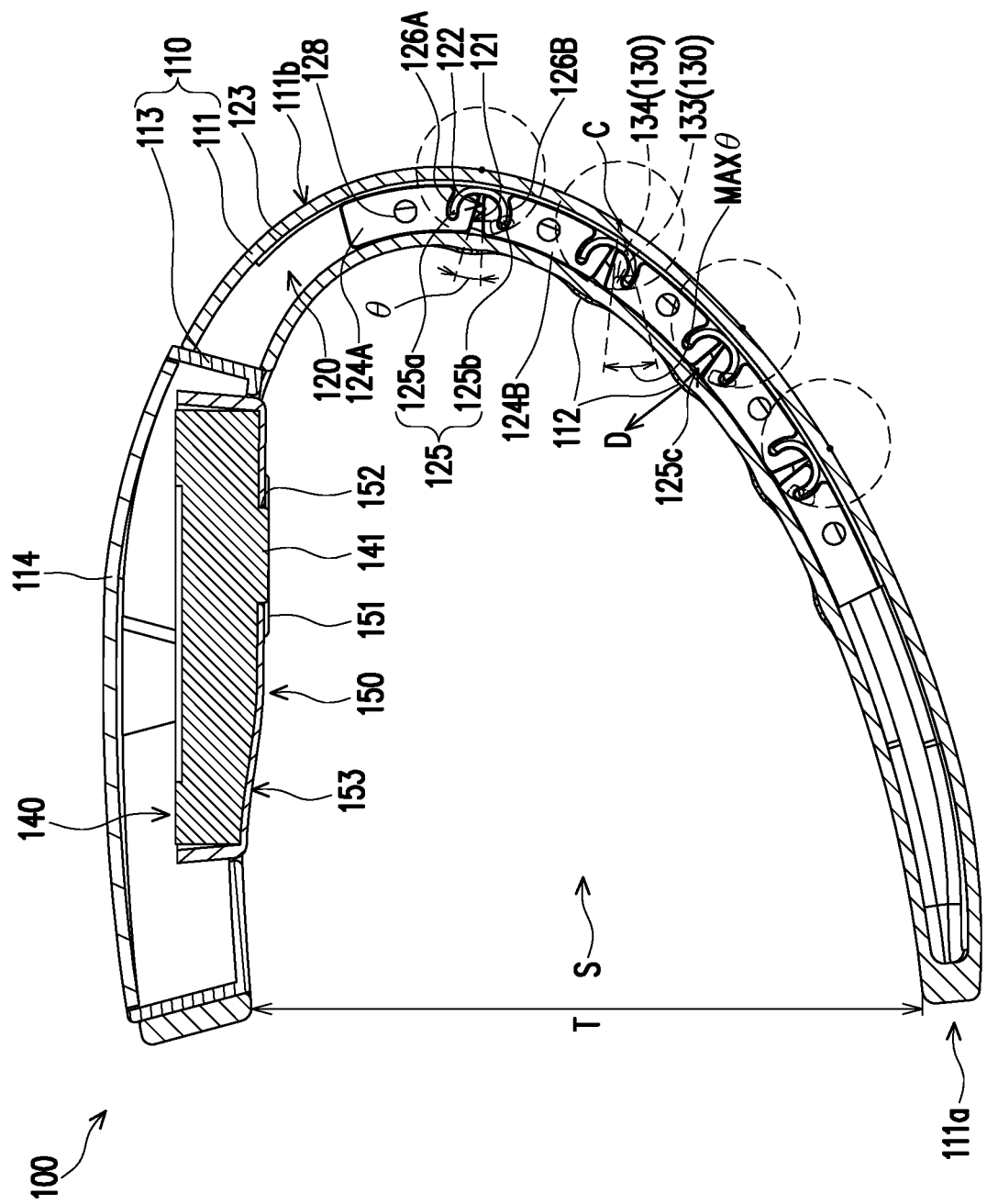
FIG. 4 is a schematic partial cross-sectional view showing the wearable physiological signal detecting device of FIG. 2.

FIG. 1 is a schematic perspective view showing a wearable physiological signal detecting device according to an embodiment of the invention. FIG. 2 is a schematic perspective view showing a first surface and a second surface of a telescopic structure of the wearable physiological signal detecting device of FIG. 1 in a second state. For clear illustration and description, part of the internal structure is shown in broken lines in FIG. 2. FIG. 3 is a schematic partial cross-sectional view showing the wearable physiological signal detecting device of FIG. 1. FIG. 4 is a schematic partial cross-sectional view showing the wearable physiological signal detecting device of FIG. 2. For clear illustration and description, part of the structure shielded behind is shown in broken lines in FIG. 3 and FIG. 4, and only part of the components is shown in the cross-sectional views in FIG. 3 and FIG. 4 to avoid interference with comprehension due to excessive cross-sectional lines. Referring to FIG. 1, FIG. 2, FIG. 3, and FIG. 4, a wearable physiological signal detecting device 100 of the present embodiment includes a device main body 110 and a telescopic structure 120. The device main body 110 has a strap 111. The strap 111 surrounds and forms a wearable space S. The wearable space S allows a user to pass his hand through to put on the device. A telescopic structure 120 is disposed inside the strap 111. The telescopic structure 120 has a plurality of first surfaces 121 and a plurality of second surfaces 122. Each first surface 121 faces a corresponding second surface 122. Each first surface 121 and the corresponding second surface 122 can continuously move close and contact each other to assume a first state as shown in FIG. 3. When the user applies a force to the strap 111, the strap 111 can be forced so that each first surface 121 and the corresponding second surface 122 move away from each other and have an angle θ to assume a second state as shown in FIG. 4.

In other words, the telescopic structure 120 is a multi-segment angle-variable structure formed of the plurality of first surfaces 121 and second surfaces 122. The state in which each first surface 121 and the corresponding second surface 122 of the telescopic structure 120 contact each other as shown in FIG. 3 is defined as the first state. The state in which each first surface 121 and the corresponding second surface 122 of the telescopic structure 120 are separated from each other to have an angle θ as shown in FIG. 4 is defined as the second state. In the first state shown in FIG. 3, the wearable space S surrounded by the strap 111 is smaller. In the second state shown in FIG. 4, the wearable space S surrounded by the strap 111 is larger. In other words, the size of the wearable space S in the second state is greater than the size of the wearable space S in the first state. Accordingly, the wearable physiological signal detecting device 100 of the invention is convenient for the user to put on or take off.

Figure 5:
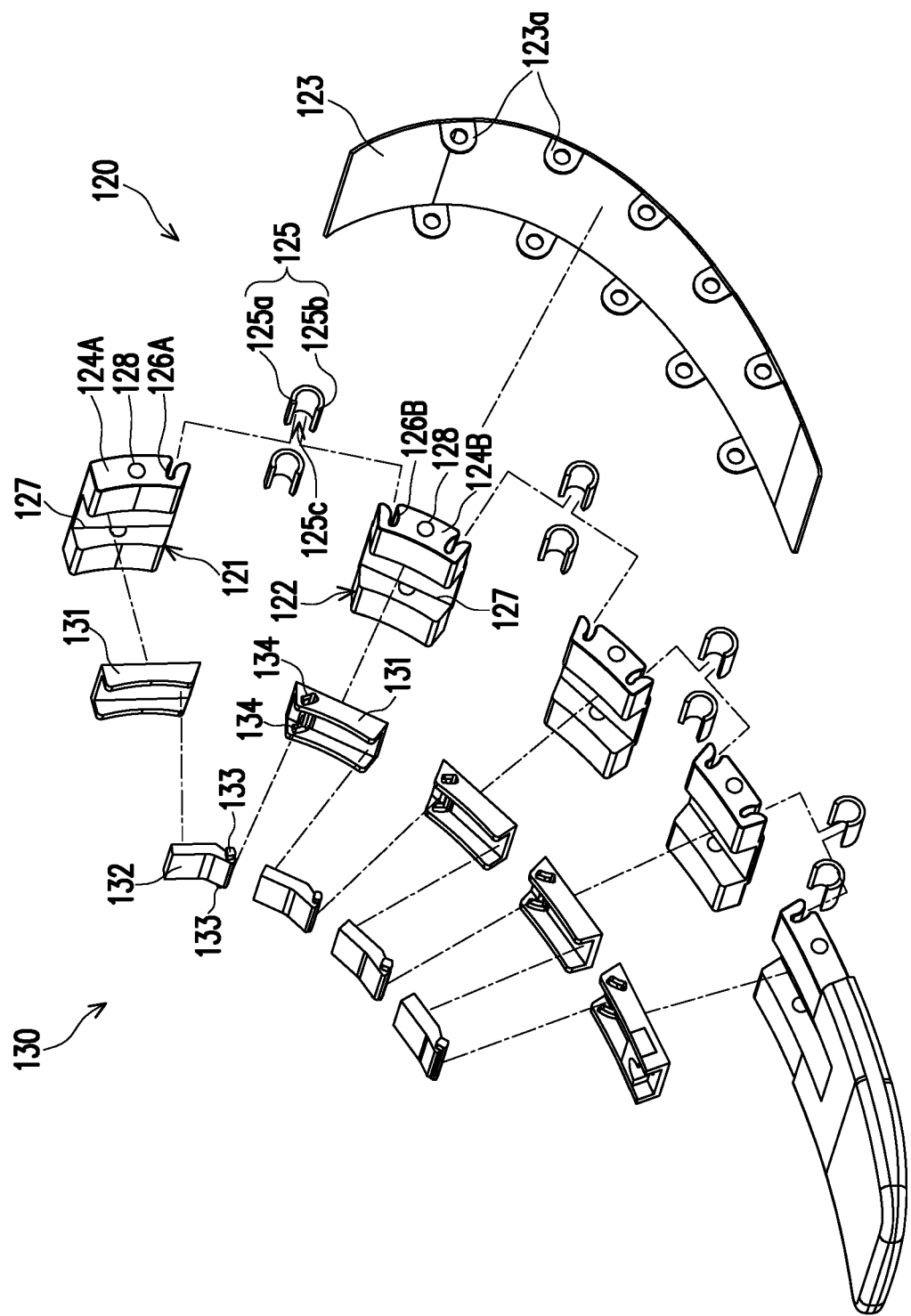
FIG. 5 is a schematic exploded view showing part of internal components of the wearable physiological signal detecting device of FIG. 2.
Figure 6:
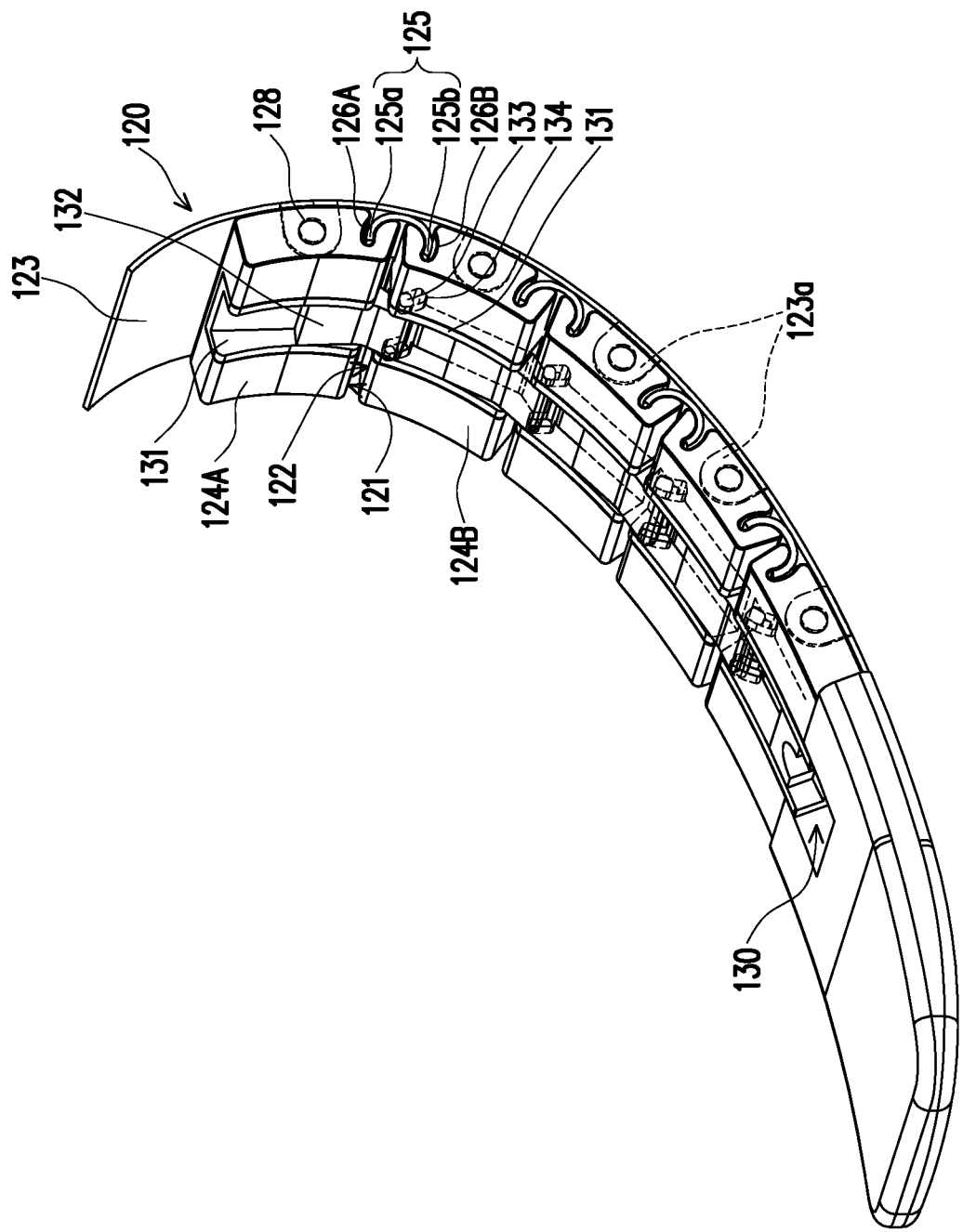
FIG. 6 is a schematic perspective view showing part of internal components of the wearable physiological signal detecting device of FIG. 2.

FIG. 5 is a schematic exploded view showing part of internal components of the wearable physiological signal detecting device of FIG. 2. FIG. 6 is a schematic perspective view showing part of internal components of the wearable physiological signal detecting device of FIG. 2. For clear illustration and description, part of the structure shielded behind is shown in broken lines in FIG. 6. Referring to FIG.

2, FIG. 3, FIG. 4, and FIG. 5, specifically, the telescopic structure 120 includes a fixing member 123, a plurality of telescopic members 124 (labeled in FIG. 2), a plurality of recovery members (for example, but not limited to, a recovery member 125), a plurality of first fixing parts (for example, but not limited to, a first fixing part 126A), and a plurality of second fixing parts (for example, but not limited to, a second fixing part 126B). The fixing member 123 is disposed in the strap 111. The telescopic members are sequentially arranged and fixed to the fixing member 123. The fixing member 123 is, but is not limited to, a metal sheet and may be used to keep the appearance smooth.

For clarity of illustration and brevity of description, the plurality of telescopic members 124 (labeled in FIG. 2) will be described by referring to one of the two adjacent telescopic members as a first telescopic member 124A (labeled in FIG. 3 and onwards) and referring to the other one of the two adjacent telescopic members as a second telescopic member 124B (labeled in FIG. 3 and onwards). The first telescopic member 124A and the second telescopic member 124B are merely expedient names for clearly distinguishing different members and are not intended to limit the invention. In addition, one set of the first surface 121, the second surface 122, the first telescopic member 124A, the second telescopic member 124B, the recovery member 125, the first fixing part 126A, and the second fixing part 126B will be described for brevity.

Referring to FIG. 3, FIG. 4, FIG. 5, and FIG. 6, in the present embodiment, the first surface 121 is disposed on the first telescopic member 124A, the second surface 122 is disposed on the second telescopic member 124B, and the first surface 121 and the second surface 122 face each other. The recovery member 125 includes a first fixing end 125a and a second fixing end 125b opposite to each other. The first fixing part 126A is disposed on the first telescopic member 124A, and the second fixing part 126B is disposed on the second telescopic member 124B. The first fixing end 125a of the recovery member 125 is connected to the first fixing part 126A, and the second fixing end 125b of the recovery member 125 is connected to the second fixing part 126B. The recovery member 125 is configured to continuously provide elastic force so that the first telescopic member 124A and the second telescopic member 124B move close to each other, and the first surface 121 located on the first telescopic member 124A and the second surface 122 located on the second telescopic member 124B can contact each other to assume the first state.

Referring to FIG. 3, FIG. 4, FIG. 5, and FIG. 6 again, the first fixing end 125a of the recovery member 125 is located between the first telescopic member 124A and the fixing member 123, and the second fixing end 125b of the recovery member 125 is located between the second telescopic member 124B and the fixing member 123. Therefore, the fixing member 123, the first telescopic member 124A, and the second telescopic member 124B can hold and fix the recovery member 125. When the recovery member 125 is stretched and deformed, the fixing member 123 is used to prevent the recovery member 125 from popping out. In the present embodiment, the recovery member 125 is, for example, a spring pin but is not limited thereto. The spring pin has an opening 125c, and the angle of the opening 125c is, for example, 120 degrees but is not limited thereto. It is noted that the angle of the opening 125c of the spring pin here refers to the angle when the spring pin is not stretched.

Accordingly, when the user wants to put on the wearable physiological signal detecting device 100 of the present embodiment, the user may apply force to the strap 111 to deform the strap 111 and the recovery member 125 to expand the wearable space S surrounded by the strap 111. At this time, the recovery member 125 will accumulate elastic force. Next, the user may put on the wearable physiological signal detecting device 100 of the present embodiment with the expanded wearable space S. Finally, when the user releases the strap 111, due to the absence of the external force, the recovery member 125 will pull each first surface 121 and each second surface 122 to contact each other to assume the first state, and the wearable physiological signal detecting device 100 can be stably worn on the user's hand. Conversely, when the user wants to take off the wearable physiological signal detecting device 100 of the present embodiment, it is only necessary to apply force to the strap 111 to deform the strap 111 and the recovery member 125 to expand the wearable space S surrounded by the strap 111, and the user can remove the wearable physiological signal detecting device 100 of the present embodiment. Therefore, the wearable physiological signal detecting device 100 of the present embodiment is convenient for the user to put on and take off.

Figure 7:
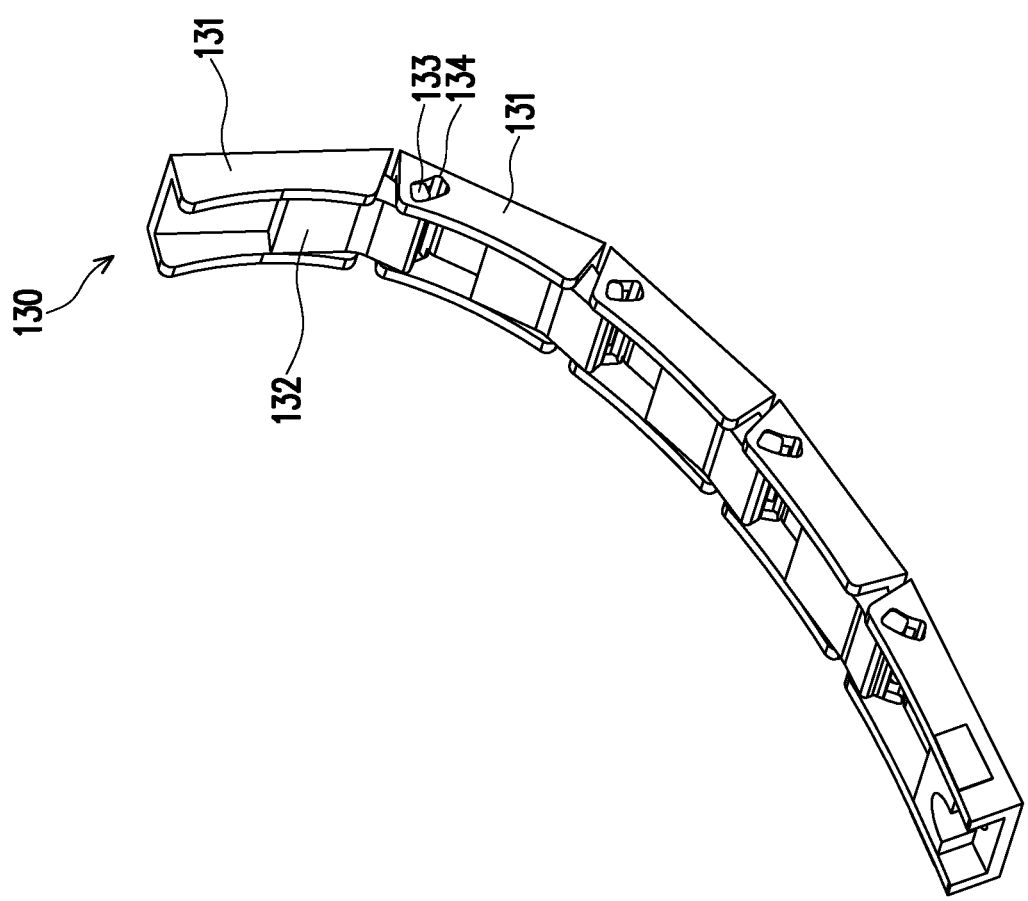
FIG. 7 is a schematic perspective view showing a limiting structure of FIG. 6.

FIG. 7 is a schematic perspective view showing a limiting structure of FIG. 6. Referring to FIG. 4, FIG. 5, FIG. 6, and FIG. 7, the wearable physiological signal detecting device 100 of the present embodiment further includes a limiting structure 130. The limiting structure 130 is disposed on the telescopic structure 120 and is configured to limit the maximum value of the angle θ when each first surface 121 and the corresponding second surface 122 assume the second state.

As shown in FIG. 5 and FIG. 6, in the telescopic structure 120, a plurality of grooves 127 may be disposed on each telescopic member for placing the limiting structure 130, and in the telescopic structure 120, a plurality of screw holes 128 may be disposed on two sides of each telescopic member. The screw hole 128 corresponds to a penetration part 123a of the fixing member 123 and allows a screw (not shown) to sequentially pass through the penetration part 123a and the screw hole 128 to thereby fix the limiting structure 130 to the telescopic structure 120. To clearly show the correspondence between the screw hole 128 and the penetration part 123a, the penetration part 123a is shown in broken lines in FIG. 6.

Specifically, the limiting structure 130 includes a plurality of groove blocks 131 (for example, but not limited to, groove blocks 131), a plurality of sliding blocks 132 (for example, but not limited to, sliding blocks 132), a plurality of limiting columns 133 (for example, but not limited to, limiting columns 133), and a plurality of limiting grooves 134 (for example, but not limited to, limiting grooves 134). Each sliding block 132 may be locked to the corresponding groove block 131 by screws (not shown). Except for the uppermost first groove block 131 in FIG. 7, each groove block 131 is provided with the limiting grooves 134 on the left and right sides. Except for the lowermost last groove block 131 in FIG. 7, each groove block 131 is provided with one sliding block 132. For the sake of brevity, only one set of the groove block 131, the sliding block 132, the limiting columns 133, and the limiting grooves 134 will be described below.

Referring to FIG. 4, FIG. 5, FIG. 6, and FIG. 7, in the present embodiment, the first telescopic member 124A and the second telescopic member 124B are both provided with the groove block 131, and the limiting grooves 134 are further disposed in the groove block 131 located on the second telescopic member 124B. The sliding block 132 is disposed on the first telescopic member 124A, and the limiting columns 133 are further disposed on the sliding block 132. Each limiting groove 134 is substantially arc-shaped and has a virtual center C of circle. As shown in FIG. 3 and FIG. 4, the virtual center C is located on an outer surface 111b of the strap 111, and the limiting column 133 is movably disposed in the limiting groove 134. The first telescopic member 124A and the second telescopic member 124B can move with respect to each other with the virtual center C as the center. Because the limiting column 133 can only move reciprocatingly between the two ends of the limiting groove 134, a maximum angle MAXθ of the reciprocating movement is the maximum value of the angle θ when the first surface 121 and the second surface 122 assume the second state. In other words, the coordination of the limiting column 133 and the limiting groove 134 can limit the maximum value of the angle θ of the telescopic structure 120 when the first surface 121 and the second surface 122 of each segment of the angle-variable structure assume the second state, so as to protect the recovery member 125 from permanent deformation and damage resulting from excessive stretching.

In the present embodiment, the maximum angle MAXθ and the angle θ are, for example but not limited to, greater than 0 degrees and less than or equal to 25 degrees. The maximum angle MAXθ and the angle θ may be 5 degrees, 10 degrees, 15 degrees, 20 degrees, 25 degrees, etc. The maximum angle MAXθ and the angle θ may specifically be 15 degrees.

In the present embodiment, an end 111a of the strap 111 is, for example, not in contact with the device main body 110 and is at a gap T from the device main body 110, but the invention is not limited thereto. When the first surface 121 and the second surface 122 assume the first state as shown in FIG. 3, the gap T is smaller. When the first surface 121 and the second surface 122 assume the second state as shown in FIG. 4, the gap T is larger.

Referring to FIG. 1, FIG. 2, FIG. 3, and FIG. 4, the wearable physiological signal detecting device 100 of the present embodiment further includes a plurality of flexible bending parts 112 disposed on the strap 111. Each flexible bending part 112 respectively shields the corresponding first surface 121 and second surface 122, is bent in a predetermined direction D opposite to the first surface 121 and the second surface 122, and is partially located in the wearable space S. When the first surface 121 and the second surface 122 assume the first state as shown in FIG. 3, the volume of the flexible bending part 112 located in the wearable space S is greater. When the first surface 121 and the second surface 122 assume the second state as shown in FIG. 4, the volume of the flexible bending part 112 located in the wearable space S is smaller.

Figure 8:
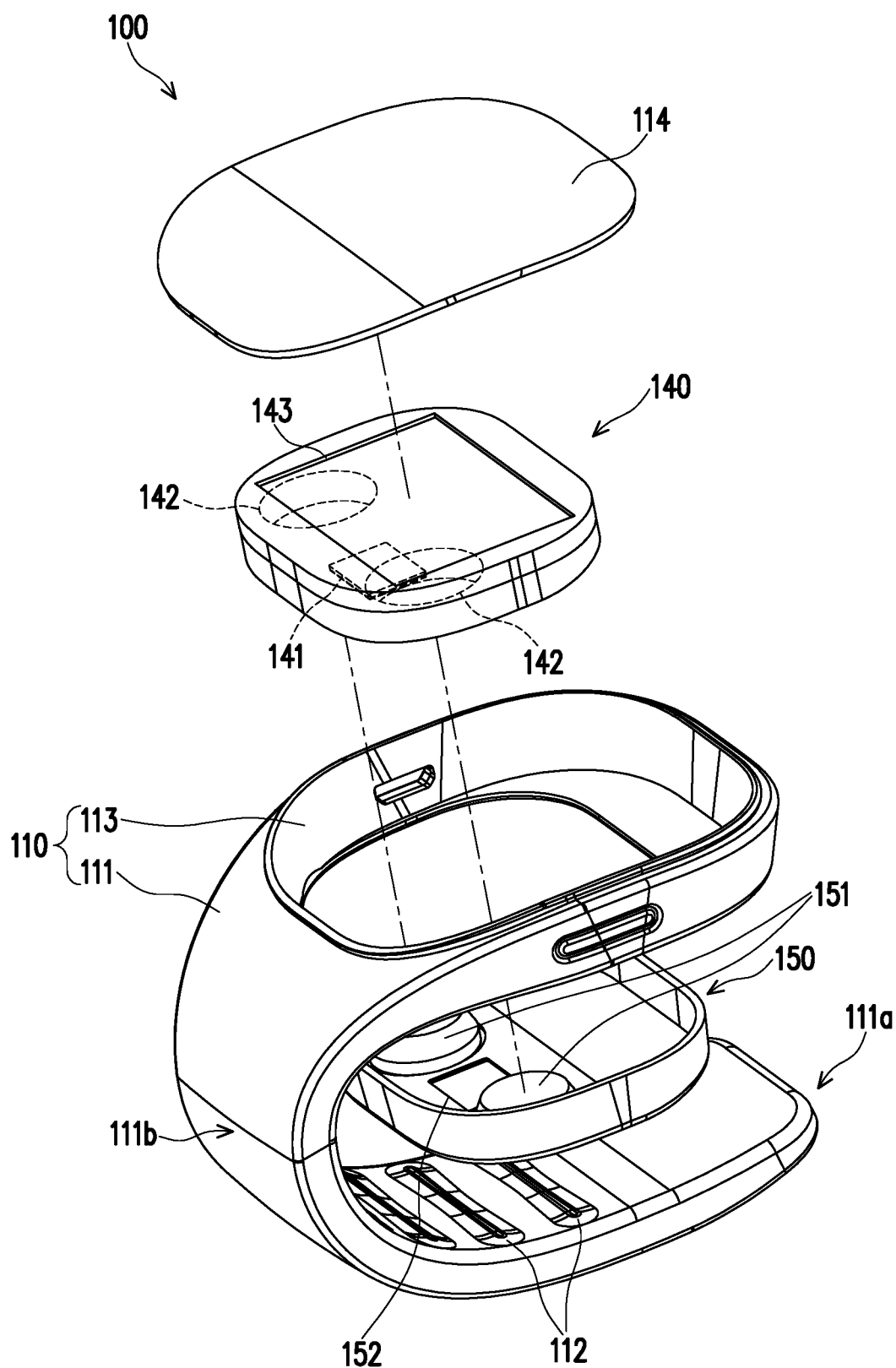
FIG. 8 is a schematic exploded view showing part of components of the wearable physiological signal detecting device of FIG. 1.
Figure 9:
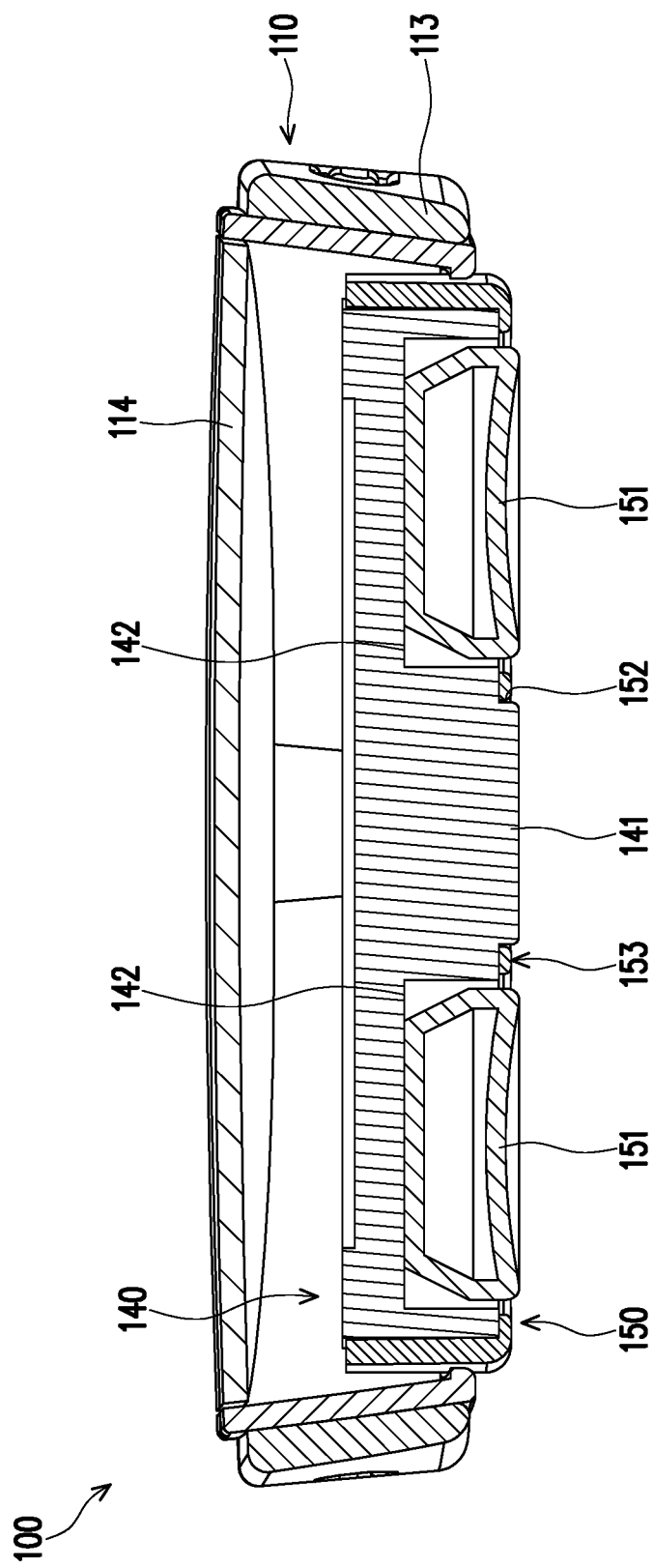
FIG. 9 is a schematic partial cross-sectional view showing the wearable physiological signal detecting device of FIG. 1.

FIG. 8 is a schematic exploded view showing part of components of the wearable physiological signal detecting device of FIG. 1. FIG. 9 is a schematic partial cross-sectional view showing the wearable physiological signal detecting device of FIG. 1. Referring to FIG. 8 and FIG. 9, the device main body 110 of the present embodiment includes an outer frame 113, the strap 111, and a transparent upper cover 114. The wearable physiological signal detecting device 100 further includes an electronic module 140 and a sensing module 150. For the sake of brevity, the electronic module 140 is schematically shown in a simple geometric form in FIG. 9, but the electronic module 140 is actually not limited to the content shown in the figure.

Specifically, the strap 111 is connected to the outer frame 113. The electronic module 140 has a first sensor 141, two accommodating spaces 142, and a display screen 143. The electronic module 140 provides, for example, a computing function, a display function, or an operation function, and may specifically include components such as a circuit board, a processor, a display panel with or without a touch function, a switch, etc. The sensing module 150 has a pair of second sensors 151, a hole 152, and a contact surface 153. The second sensors 151 may be accommodated in the two accommodating spaces 142. The hole 152 and the wearable space S communicate with each other. The first sensor 141 may pass through the hole 152, so that the first sensor 141 and the pair of second sensors 151 can be partially located in the wearable space S to contact the user's skin, so as to obtain physiological signals of the user such as, but not limited to, the blood pressure, the pulse, the blood flow rate, etc. and then convert them into physiological signal information of the user such as, but not limited to, the heartbeat, the blood flow rate, the blood pressure, the blood vessel wall thickness, the blood concentration, etc.

In the present embodiment, the surface of the first sensor 141 located in the wearable space S and the surfaces of the pair of second sensors 151 located in the wearable space S are flush with each other so as to evenly contact the user's skin. The contact surface 153 between the sensing module 150 and the user may be provided with an airtight member made of materials such as a soft gel, a hydrogel, etc. to enhance the airtightness between the sensing module 150 and the user's skin, which thereby improves the detection accuracy of the first sensor 141 and the second sensors 151 and at the same time provides the waterproof performance of the sensing module 150.

In the present embodiment, the first sensor 141 is, for example, a sensor sensing the heartbeat, the blood flow rate, the blood pressure, the blood vessel wall thickness, and/or the blood concentration, but the invention is not limited thereto. The second sensor 151 is, for example, a sensor sensing the heartbeat, the blood flow rate, the blood pressure, the blood vessel wall thickness, and/or the blood concentration, but the invention is not limited thereto. The types, quantities, and configuration methods of the first sensor 141 and the second sensor 151 are merely illustrative and are not intended to limit the invention. In addition, the physiological signals of the user that may be detected by the first sensor 141 and the second sensor 151, and the physiological signal information of the user that may be converted and obtained may be appropriately adjusted according to the requirements and are not specifically limited herein.

In the present embodiment, the sensing module 150 and the electronic module 140 are fixed to each other and electrically connected to each other, and the sensing module 150 and the electronic module 140 are further fixed to the outer frame 113 of the device main body 110. In other words, the sensing module 150, the electronic module 140, and the device main body 110 of the present embodiment may be fixed as a single component, which is suitable for use in daily life, sports, and other occasions by general users.

In other embodiments, the electronic module may be fixed to the outer frame to be integrated, and the sensing module may be detachably fixed by means of snap-fits, through holes, etc. and electrically connected. Since the sensing module needs to be in constant contact with the user's skin, by designing the sensing module as a disposable component, medical and hygienic safety can be improved. In addition, the first sensor on the electronic module may also be reused through disinfection and other methods, which can also improve medical and hygienic safety.

In other embodiments, the sensing module may be detachably fixed by means of snap-fits, through holes, etc. and electrically connected to the electronic module. Similarly, both the sensing module and the electronic module may be further detachably fixed to the outer frame of the device main body by means of snap-fits, through holes, etc. Since the sensing module needs to be in constant contact with the user's skin, by designing the sensing module as a disposable component, medical and hygienic safety can be improved. In addition, the first sensor on the electronic module may be reused through disinfection and other methods, or the electronic module may also be used as a disposable component, which can also improve medical and hygienic safety.

In summary of the above, in the wearable physiological signal detecting device of the invention, the strap surrounds and forms a wearable space. The wearable space allows the user to pass his hand through to put on the device. The telescopic structure is disposed inside the trap. The telescopic structure has a plurality of first surfaces and a plurality of second surfaces. Each first surface faces the corresponding second surface. Each first surface and the corresponding second surface can continuously move close and contact each other to assume a first state. When the user applies force to the strap, the strap can be forced so that each first surface and the corresponding second surface move away from each other and have an angle to assume a second state. The size of the wearable space in the second state is greater than the size of the wearable space in the first state. Thereby, the wearable physiological signal detecting device of the invention is convenient for the user to put on or take off.

In addition, the electronic module and the sensing module of the invention contribute to improving medical and hygienic safety.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A wearable physiological signal detecting device, comprising:
    an electronic module having a first sensor, and the first sensor is configured to detect a physiological signal;
    a device main body having a strap, wherein the strap surrounds a wearable space; and
    an expandable structure, disposed in the strap and having a plurality of first surfaces and a plurality of second surfaces, wherein each of the first surfaces faces a corresponding second surface, each of the first surfaces and the corresponding second surface are adapted to continuously move close and contact each other to assume a first state, the strap is adapted to be forced so that each of the first surfaces and the corresponding second surface move away from each other and each of the first surfaces have an angle relative to the corresponding second surface to assume a second state,
    wherein a size of the wearable space when each of the first surfaces and the corresponding second surface assume the second state is greater than a size of the wearable space when each of the first surfaces and the corresponding second surface assume the first state, wherein in the first state, each of the first surfaces and the corresponding second surface are parallel to each other, and in the second state, each of the first surfaces and the corresponding second surface are not parallel to each other,
    the expandable structure comprises:
        a fixing member disposed in the strap;
        a plurality of expandable members sequentially arranged and fixed to the fixing member, wherein each of the first surfaces is provided on one of two adjacent expandable members, and each of the second surfaces is provided on the other one of the two adjacent expandable members; and
    a plurality of spring pins, respectively connected between two adjacent expandable members and continuously providing elasticity so that each of the first surfaces and the corresponding second surface which are adjacent to each other assume the first state, wherein a part of each of the spring pins is located between one of two adjacent expandable members and the fixing member, and another part of each of the spring pins is located between the other one of the two adjacent expandable members and the fixing member,
    wherein a spring pin of the plurality of spring pins has an opening.

2. The wearable physiological signal detecting device according to claim 1, wherein each of the spring pins respectively comprises a first fixing end and a second fixing end opposite to each other, and the expandable structure further comprises:
    a plurality of first fixing parts respectively disposed on one of two adjacent expandable members, wherein each of the first fixing ends is connected to the corresponding first fixing part and is located between the one of the two adjacent expandable members and the fixing member; and
    a plurality of second fixing parts respectively disposed on the other one of the two adjacent expandable members, wherein each of the second fixing ends is connected to the corresponding second fixing part and is located between the other one of the two adjacent expandable members and the fixing member.

3. The wearable physiological signal detecting device according to claim 1, wherein an angle of the opening is 120 degrees.

4. The wearable physiological signal detecting device according to claim 1, further comprising:
    a limiting structure, disposed on the expandable structure and configured to limit a maximum value of the angle when each of the first surfaces and the corresponding second surface assume the second state.

5. The wearable physiological signal detecting device according to claim 4, wherein the expandable structure comprises a plurality of sequentially arranged expandable members, each of the first surfaces is provided on one of two adjacent expandable members, each of the second surfaces is provided on the other one of the two adjacent expandable members, and the limiting structure comprises:
    a plurality of groove blocks respectively disposed on each of the expandable members;
    a plurality of sliding blocks respectively disposed on one of two adjacent expandable members;
    a plurality of limiting columns, respectively disposed to a corresponding sliding block; and
    a plurality of limiting grooves respectively provided in the groove block located on the other one of the two adjacent expandable members,
    wherein each of the limiting columns is movably disposed in a corresponding limiting groove to limit the maximum value of the angle when each of the first surfaces and the corresponding second surface assume the second state.

6. The wearable physiological signal detecting device according to claim 5, wherein each of the limiting grooves is arc-shaped and defines a virtual center of a circle, and the virtual center of the circle is located on an outer surface of the strap.

7. The wearable physiological signal detecting device according to claim 1, wherein the angle is greater than 0 degrees and less than or equal to 25 degrees.

8. The wearable physiological signal detecting device according to claim 1, wherein an end of the strap is not in contact with the device main body and is at a gap from the device main body, and a size of the gap when each of the first surfaces and the corresponding second surface assume the second state is greater than a size of the gap when each of the first surfaces and the corresponding second surface assume the first state.

9. The wearable physiological signal detecting device according to claim 1, wherein the device main body has a plurality of flexible bending parts respectively disposed on the strap, partially located in the wearable space, and respectively shielding the first surface and the corresponding second surface which are adjacent to each other,
wherein a volume of each of the flexible bending parts located in the wearable space when each of the first surfaces and the corresponding second surface assume the first state is greater than a volume of each of the flexible bending parts located in the wearable space when each of the first surfaces and the corresponding second surface assume the second state.

10. The wearable physiological signal detecting device according to claim 1, wherein the device main body comprises an outer frame, and both of the strap and the electronic module connected to the outer frame, and the wearable physiological signal detecting device further comprises:
a sensing module, connected to the outer frame and the electronic module and having a pair of second sensors and a hole, wherein the hole communicates with the wearable space,
wherein the first sensor passes through the hole, and the first sensor and the pair of second sensors are partially located in the wearable space.

11. The wearable physiological signal detecting device according to claim 10, wherein a surface of the first sensor located in the wearable space and surfaces of the pair of second sensors located in the wearable space are flush with each other.

12. The wearable physiological signal detecting device according to claim 10, wherein the electronic module is fixed to the outer frame, and the sensing module is fixed to the outer frame and the electronic module.

13. The wearable physiological signal detecting device according to claim 10, wherein the electronic module is fixed to the outer frame, and the sensing module is detachably disposed on the outer frame and the electronic module.

14. The wearable physiological signal detecting device according to claim 10, wherein the electronic module is detachably disposed on the outer frame, and the sensing module is detachably disposed on the outer frame and the electronic module.

* * * * *